US00PP13150P2

(12) United States Plant Patent
Hammett

(10) Patent No.: US PP13,150 P2
(45) Date of Patent: Oct. 29, 2002

(54) HELIANTHUS PLANT NAMED 'FIRST LIGHT'

(76) Inventor: Keith Richard William Hammett, 488c, Don Buck Road, Massey, Auckland 8 (NZ)

( * ) Notice: Subject to any disclaimer, the term of this patent is extended or adjusted under 35 U.S.C. 154(b) by 0 days.

(21) Appl. No.: 09/904,728

(22) Filed: Jul. 16, 2001

(51) Int. Cl.[7] ..... A01H 5/00

(52) U.S. Cl. ..... Plt./263

(58) Field of Search ..... Plt./263

(56) References Cited

PUBLICATIONS

UPOV–ROM GTITM Computer Database, 2001/06, GTI Jouve Retrieval Software, Citation for 'First Light'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Helianthus plant named 'First Light', characterized by its erect and spiked plant habit; freely basal branching habit; dense and full plants; freely flowering habit; daisy-type inflorescences with bright yellow ray florets and dark brown disc florets; and good garden performance.

1 Drawing Sheet

BOTANICAL CLASSIFICATION

*Helianthus salicifolius.*

VARIETY DENOMINATION

'First Light'.

BACKGROUND OF THE INVENTION

The present invention relates to a new and distinct cultivar of Helianthus plant, botanically known as *Helianthus salicifolius* and hereinafter referred to by the name 'First Light'.

The new cultivar is a product of a planned breeding program conducted by the Inventor in Massey, Auckland, New Zealand. The objective of the breeding program is to create new Helianthus cultivars having compact plant habit and good garden performance.

The new Helianthus originated from a cross made by the Inventor in 1992, in Massey, Auckland, New Zealand, of the Helianthus cultivar Golden Pyramid, not patented, as the female, or seed, parent with the Helianthus cultivar Autumn Glory, not patented, as the male, or pollen, parent. The new Helianthus was discovered and selected by the Inventor as a single flowering plant within the progeny of the stated cross grown in a controlled environment in Massey, Auckland, New Zealand in 1992. The selection of this plant was based on its compact plant habit and good garden performance.

Asexual reproduction of the new cultivar by terminal cuttings taken in a controlled environment in Massey, Auckland, New Zealand since 1993, has shown that the unique features of this new Helianthus are stable and reproduced true to type in successive generations.

SUMMARY OF THE INVENTION

The cultivar First Light has not been observed under all possible environmental conditions. The phenotype may vary somewhat with variations in environment such as temperature, daylength, light intensity, water status and fertilizer rate and type without, however, any variance in genotype.

The following traits have been repeatedly observed and are determined to be the unique characteristics of 'First Light'. These characteristics in combination distinguish 'First Light' as a new and distinct cultivar:

1. Erect and spiked growth habit.
2. Freely basal branching habit; dense and full plants.
3. Long linear leaves.
4. Freely flowering habit.
5. Daisy-type inflorescences with bright yellow ray florets and dark brown disc florets.
6. Good garden performance.

Plants of the new Helianthus can be compared to plants of the female parent, the cultivar Golden Pyramid. In side-by-side comparisons conducted by the Inventor in Massey, Auckland, New Zealand, California, plants of the new Helianthus differ from plants of the cultivar Golden Pyramid in the following characteristics:

1. Plants of the new Helianthus are more compact than plants of the cultivar Golden Pyramid.
2. Plants of the new Helianthus have shorter internodes than plants of the cultivar Golden Pyramid.
3. Plants of the new Helianthus have slightly lighter ray floret color than plants of the cultivar Golden Pyramid.

Plants of the new Helianthus can be compared to plants of the female parent, the cultivar Autumn Glory. In side-by-side comparisions conducted by the Inventor in Massey, Auckland, New Zealand, plants of the new Helianthus differ from plants of the cultivar Autumn Glory in the following characteristics:

1. Plants of the new Helianthus are much more compact than plants of the cultivar Autumn Glory.
2. Plants of the new Helianthus have much shorter internodes than plants of the cultivar Autumn Glory.

3. Plants of the new Helianthus have slightly lighter ray floret color than plants of the cultivar Autumn Glory.

Compared to plants of the cultivar Low Down, disclosed in U.S. Plant patent application Ser. No. 09/904,727 filed concurrently, plant of the new Helianthus are taller, have longer leaves, and have larger inflorescences.

Plants of the new Helianthus can be compared to plants of the cultivar Table Mountain, not patented. In side-by-side comparisons conducted by the Inventor in Massey, Auckland, New Zealand, plants of the new Helianthus differ from plants of the cultivar Table Mountain in the following characteristics:

1. Plants of the new Helianthus have an erect spiked habit whereas plants of the cultivar Table Mountain have a flattopped habit.

2. Plants of the new Helianthus have slightly lighter ray floret color than plants of the cultivar Table Mountain.

BRIEF DESCRIPTION OF THE PHOTOGRAPH

The accompanying photograph illustrates the overall appearance of the new Helianthus. This photograph shows the colors as true as it is reasonably possible to obtain in colored reproductions of this type. Colors in the photograph may differ slightly from the color values cited in the detailed botanical description which accurately describe the colors of the new Helianthus. The photograph comprises a side perspective view of a typical flowering plant of 'First Light' that was about six months old.

DETAILED BOTANICAL DESCRIPTION

In the following description, color references are made to The Royal Horticultural Society Colour Chart, 1995 edition, except where general terms of ordinary dictionary significance are used. The following observations and measurements describe plants grown in one-gallon containers in Lancaster, Pa., under conditions which approximate those generally used in container Helianthus production. Plants were grown under natural season conditions in polyethylene-covered greenhouses during the summer and fall. During the flowering period, day temperatures were about 85° F. and night temperatures were about 70 to 75° F. Measurements and numerical values represent averages for typical flowering plants that were about 6 months old.

Botanical classification: *Helianthus salicifolius* cultivar First Light.

Parentage:

*Female, or seed, parent.*—*Helianthus salicifolius* cultivar Golden Pyramid, not patented.

*Male, or pollen, parent.*—*Helianthus salicifolius* cultivar Autumn Glory, not patented.

Propagation:

*Type.*—Terminal tip cuttings.

*Time to initiate roots.*—Summer: About 14 days at 20° C. Winter: About 21 days at 20° C.

*Root description.*—Whitish, fine and fibrous.

*Rooting habit.*—Freely branching, dense.

Plant description:

*Appearance.*—Perennial herbaceous daisy-type container Helianthus. Inverted triangle; erect growth habit and compact plant habit. Stems mostly upright giving a spiked appearance to the plant. Freely basal branching with about 25 to 30 branches per plant.

*Plant height.*—About 44 cm.

*Plant diameter.*—About 42 cm.

*Basal branches.*—Length: About 44 cm. Diameter: About 4 mm. Internode length: About 6.5 mm. Aspect: Erect. Texture: Pubescent, rough. Color: 146C.

*Foliage description.*—Leaf arrangement: Alternate. Length: About 9.5 cm. Width: About 7 mm. Apex: Acute. Base: Attenuate; sessile. Margin: Entire. Texture: Upper surface: Pubescent, rough. Lower surface: Densely pubescent. Color: Young and fully expanded foliage, upper surface: More green than 147A. Young and fully expanded foliage, lower surface: 147C to 147D. Venation, both surfaces: Close to 150D.

Inflorescence description:

*Appearance.*—Daisy-type inflorescence form with elongated oblong-shaped ray florets. Inflorescences borne on terminals above the foliage arising from leaf axils. Disk and ray florets arranged acropetally on a capitulum. About three to six inflorescences per lateral.

*Flowering response.*—Plants flower under periods of long days/short nights, typically during the late summer, and continue to flower for about 2 months.

*Inflorescence bud* (*before showing color*).—Length: About 6 mm. Diameter: About 8 mm. Shape: Flattened sphere. Phyllary color: Close to 143A.

*Inflorescence size.*—Diameter: About 7.1 cm. Depth (height): About 1.5 cm. Disc diameter: About 1.3 cm. Receptacle diameter: About 8 mm.

*Ray florets.*—Shape: Elongate oblong. Length: About 3.5 cm. Corolla tube length: About 2 mm. Width: About 9 mm. Apex: Emarginate. Margin: Entire. Texture: Smooth, satiny. Orientation: Initially upright, then close to 90° from vertical. Number of ray florets per inflorescence: About 16 in a single row. Color: When opening, upper surface: 14A. When opening, lower surface: 12A. Opened inflorescence, upper surface: 13B; color does not fade with subsequent development. Opened inflorescence, lower surface: 12A.

*Disc florets.*—Shape: Tubular with pointed apices Length: About 6 mm. Width: Apex: About 1.5 mm. Base: About 1 mm. Number of disc florets per inflorescence: About 82. Color: Immature: 144A. Mature: Apex: Close to 200A. Mid-section: 144A to 11B. Base: 154A to 155D.

*Phyllaries.*—Quantity per inflorescence: About 28 in two rows. Length: About 8.5 mm. Width: About 1.5 mm. Shape: Linear with acute apex. Texture: Pubescent, rough. Color, both surfaces: 144A.

*Peduncle.*—Aspect: Erect. Strength: Strong, wiry, flexible. Length: First peduncle: About 3.4 cm. Fourth peduncle: About 2.7 cm. Seventh peduncle: About 2 cm. Diameter: About 1.5 mm. Texture: Pubescent, rough. Color: 144A to 144B.

*Reproductive organs.*—Androecium: Present on disc florets only. Anther color: 15A. Pollen: Scarce. Pollen color: 21A. Gynoecium: Present on both ray and disc florets.

*Seed.*—Seed production has not been observed.

Disease/pest resistance: Plants of the new Helianthus have not been shown to be resistant to pathogens or pests common to Helianthus.

Garden performance: Plants of the new Helianthus have been observed to be tolerant to rain and wind. Plants of the new Helianthus have been observed to tolerate temperatures from about 10 to 20° F. to about 120° F.

It is claimed:

1. A new and distinct cultivar of Helianthus plant named 'First Light', as illustrated and described.

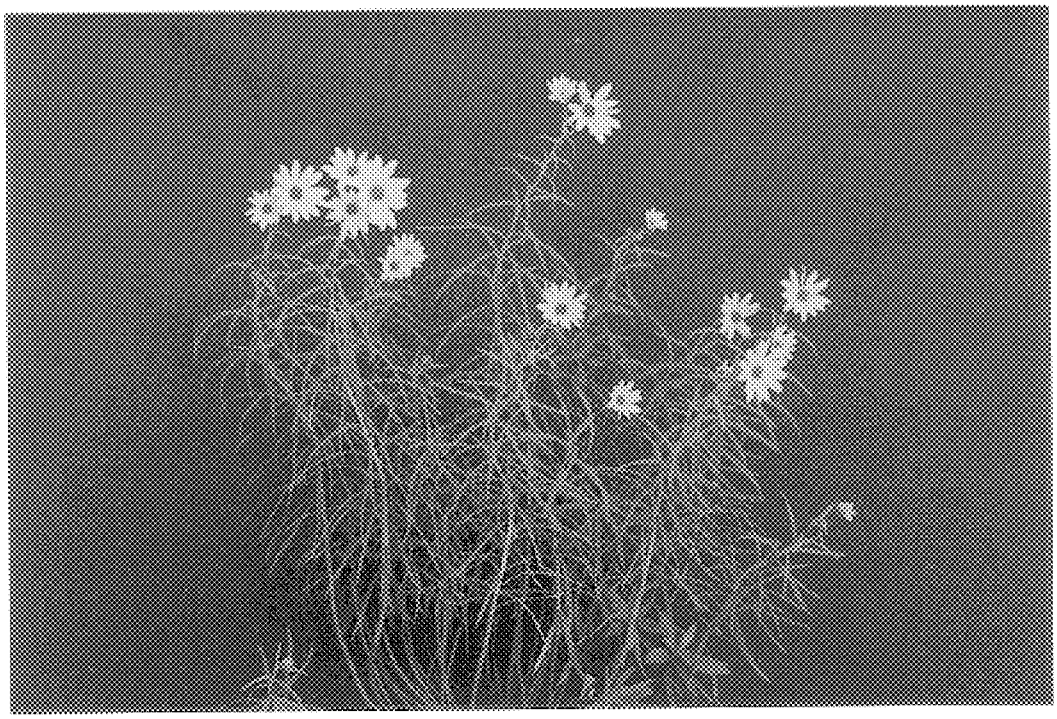

* * * * *